(12) United States Patent
Liang et al.

(10) Patent No.: US 6,234,029 B1
(45) Date of Patent: May 22, 2001

(54) TESTING MODULE FOR TESTING THE STRENGTH OF THE WELDING AREA ON A PCB

(75) Inventors: Ming-Shuoh Liang, Kaohsiung; Sung-Ching Hung, Changhwa Hsien; Hung-Nan Chen, Kaohsiung Hsien; Simon Lee, Tainan, all of (TW)

(73) Assignee: Advanced Semiconductor Engineering, Inc., Kaohsiung (TW)

( * ) Notice: Subject to any disclaimer, the term of this patent is extended or adjusted under 35 U.S.C. 154(b) by 0 days.

(21) Appl. No.: 09/383,440

(22) Filed: Aug. 27, 1999

(51) Int. Cl.[7] ........................................ G01N 3/20
(52) U.S. Cl. ................................ 73/850; 73/856
(58) Field of Search ..................... 73/150 A, 819, 73/824, 827, 842, 850, 853, 856, 862.041, 862.042, 862.043, 862.046

(56) References Cited
U.S. PATENT DOCUMENTS

| | | | |
|---|---|---|---|
| 4,677,856 | * 7/1987 | Fischer | .................................... 73/850 |
| 5,355,683 | * 10/1994 | Taylor | .................................... 73/856 |
| 5,438,863 | * 8/1995 | Johnson | .............................. 73/150 A |
| 5,712,431 | * 1/1998 | Vilendrer | ............................... 73/853 |
| 5,811,686 | * 9/1998 | Lavoie et al. | ............................ 73/856 |
| 5,948,994 | * 9/1999 | Jen et al. | ............................... 73/856 |

\* cited by examiner

Primary Examiner—Benjamin R. Fuller
Assistant Examiner—Maurice Stevens
(74) Attorney, Agent, or Firm—Rosenberg, Klein & Lee

(57) ABSTRACT

A testing module for testing the strength of the welding area on a PCB is disclosed. The testing module has a plurality of first plates each provided with a plurality of pressing plates adjustably mounted thereon and a plurality of second plates each provided with a plurality of supporting plates securely mounted thereon. Each of the pressing plates are located at the center of two adjacent supporting plates, such that a plurality of PCBs are able to be tested for the strength of the welding area at a time.

10 Claims, 9 Drawing Sheets

TESTING MODULE FOR TESTING THE STRENGTH OF THE WELDING AREA ON A PCB

BACKGROUND OF THE INVENTION

1. Field of the Invention

The present invention relates to a testing module for a printed circuit board (PCB), and more particularly to a testing module for testing the strength of the welding area on the PCB.

2. Description of Related Art

Basically, there are several ways of connection between a printed circuit board (PCB) and a surface mounted device. The first method of connecting a PCB (10) and a surface mounted device (11) is by means of connecting feet, as shown in FIG. 7. It is to be noted that the connecting feet are welded on the face of the PCB (10). The second method is by solder balls (111), which are used to connect the surface mounted device (11) with a ball grid array (BGA), as shown in FIG. 8. Another commonly seen method of connecting a surface mounted device (11) to a PCB (10) is by what is called "surface welding", as shown in FIG. 9.

The reason of the surface mounted device (11) being securely mounted on the PCB (10) is after the surface mounted device (11) is secured in relation to the PCB (10), the press of a user on a random key will activate a specific circuit or a loop on the PCB (10). When the press is gone or another key is pressed to activate other circuit or loop on the PCB (10), the activation to the PCB (10) will be terminated. However, the press of a user on the key will always apply a force to the PCB (10) and will deform the PCB (10) accordingly, as shown in FIG. 12. Once the PCB (10) is permanently deformed, the connecting areas between the PCB (10) and the surface mounted device (11) will have the largest stress. As the frequency of using the PCB increases, the PCB (10) may become damaged or even break at the connecting area with the surface mounted device (11). Therefore, if the number of times that the PCB (10) can be bent is available, it is possible to know the life span of the PCB (10), and the user will know when he/she should proceed maintenance under normal operation to the PCB (10).

FIG. 10 and FIG. 11 show two kinds of conventional testing modules (20,30) for testing the strength of the welding area between a surface mounted device (11) and the PCB (10). The testing module (20,30) includes a base (21,31) having a T-shaped slot (22,32) defined therein, a pair of spaced and opposed supporting plates (23,33) movably secured on the base (21,31) by the slot (22,32) and a pressing block (24,34) reciprocally movable in relation to the pair of supporting plates (23,33). With such an arrangement, the PCB (10) is able to be placed between the pair of supporting plates (23,33) and the pressing block (24,34) controlled by a computerized device is able to apply a force to the PCB (10) placed between the pair of supporting plates (23,33). The PCB (10) after being applied a force thereon will be bent accordingly, as shown in FIG. 12. Meanwhile, a resistance indicator (not shown) is connected to the connecting area between the PCB (10) and the surface mounted device (11) to monitor the resistance therebetween. When an infinite large resistance is shown on the resistance indicator, a breakage between the PCB (10) and the surface mounted device (11) may occur. That is, a user is able to know the maximum load the connecting area between the PCB (10) and the surface mounted device (11) has and accordingly the number of times the PCB (10) can be bent.

However, using such a testing module can only test one PCB at a time, which is inefficient and time consuming.

To overcome the shortcomings, the present invention tends to provide an improved testing module for testing the strength of a welding area on a PCB to mitigate and/or obviate the aforementioned problems.

SUMMARY OF THE INVENTION

The main objective of the invention is to provide an improved testing module for testing the strength of a welding area on a PCB. The testing module has a plurality of supporting plates arranged in lines and a plurality of pressing blocks each arranged between two adjacent supporting plates. Therefore, the testing module of the invention is able to test several PCBs at a time, which is time saving and effective.

Other objects, advantages and novel features of the invention will become more apparent from the following detailed description when taken in conjunction with the accompanying drawings.

DETAILED DESCRIPTION OF PREFERRED EMBODIMENT

Figure 1:
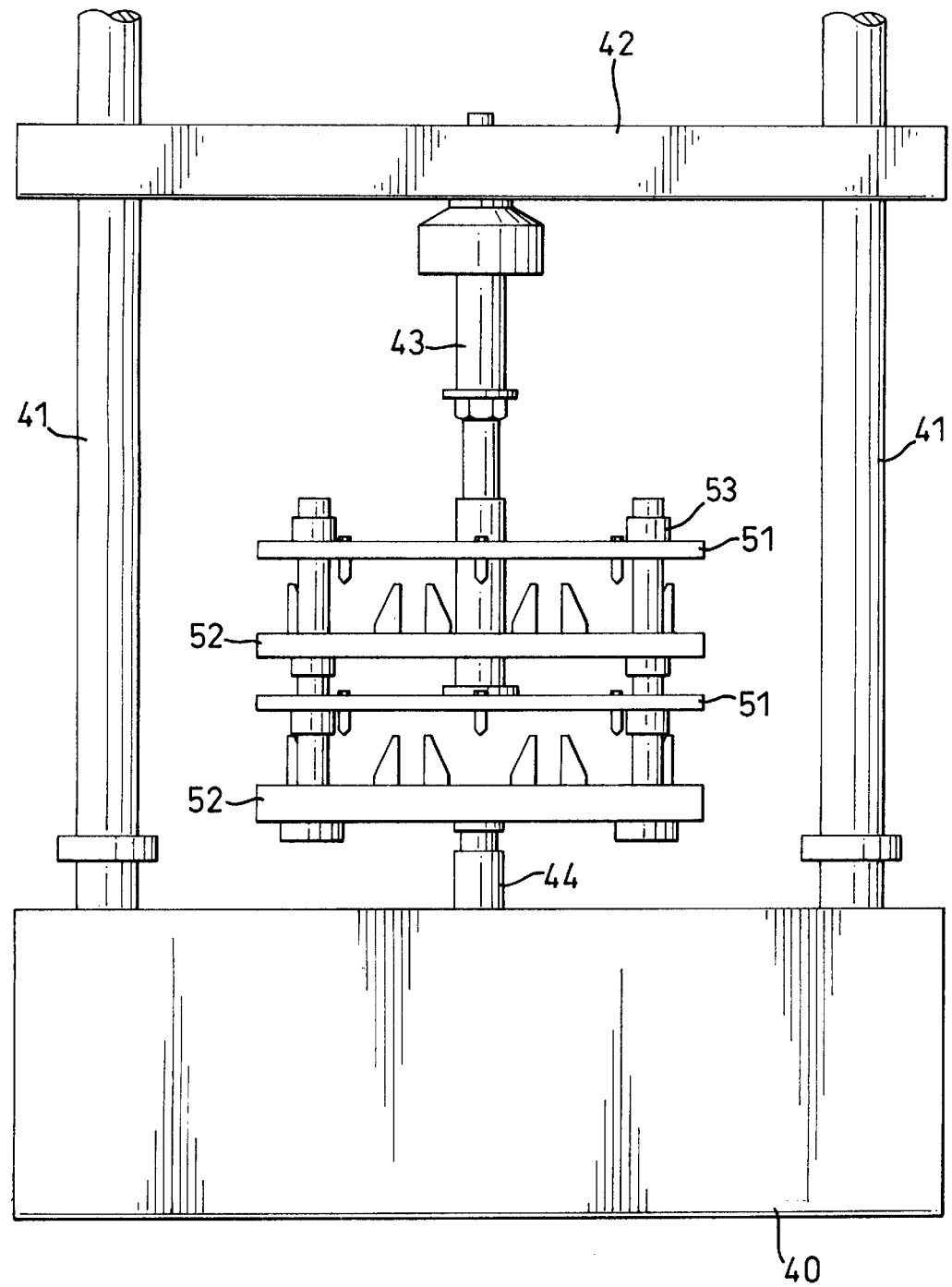
FIG. 1 is a plan view showing the arrangement of the testing module of the invention.

Referring to FIG. 1, a testing module for testing the welding area on a PCB and constructed in accordance with the present invention is shown. The testing module of the invention includes a base (40), two posts (41) integrally extended outward from the base (40), a top plate (42) slidably mounted between the two posts (41) and being opposite to the base (40), a main shaft (43) integrally formed and extended from a bottom face of the top plate (42), a secondary shaft (44) integrally formed and extended from a top face of the base (40) and a plurality of sets of first plates (51) and second plates (52).

Figure 2:
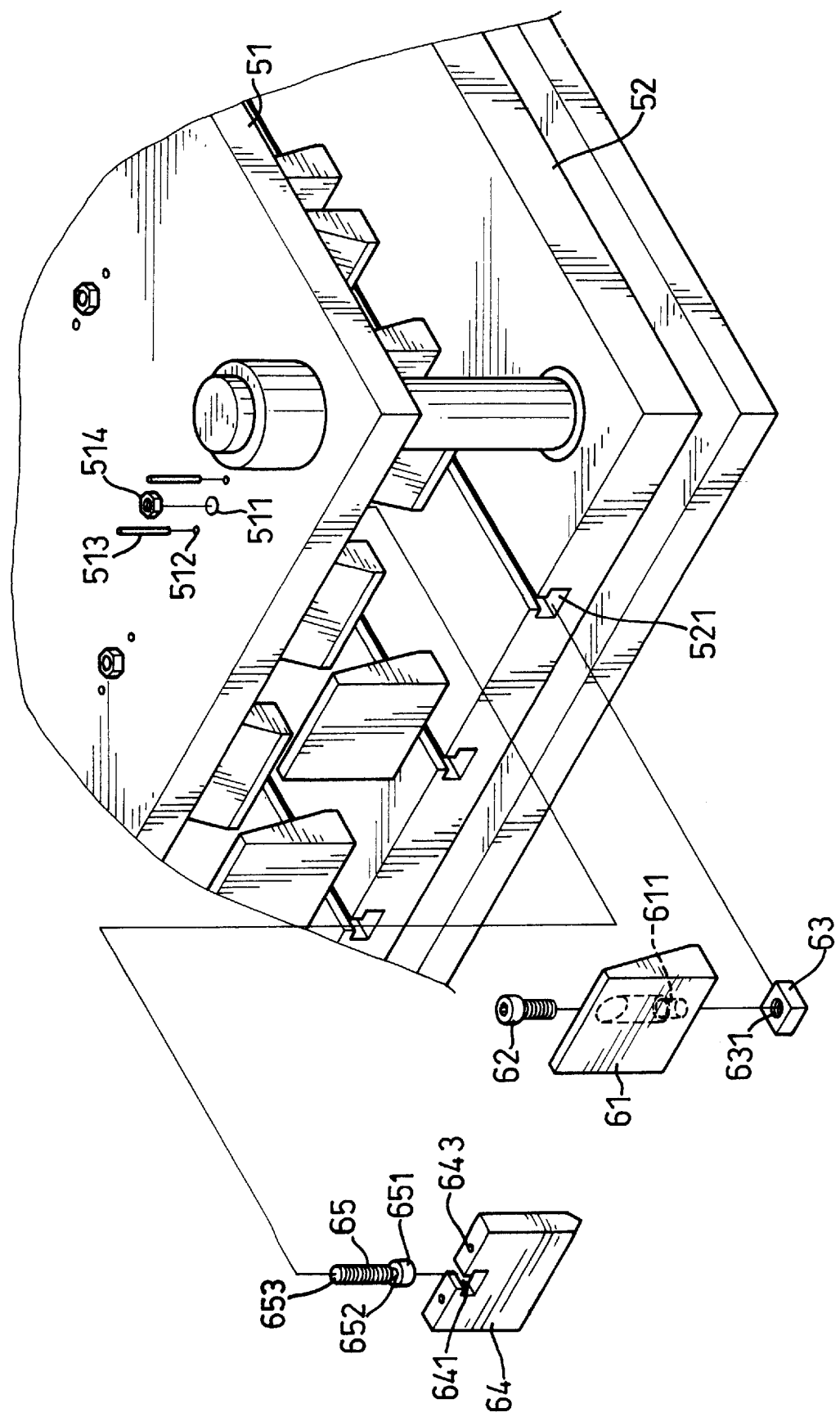
FIG. 2 is a partial exploded perspective view showing the connection relationship among the supporting plate, the pressing plate and the upper and lower plates of the testing module of the invention.

Referring to FIG. 2 and taking FIG. 1 for reference, it is to be noted that two sets of first and second plates (51,52) are provided to the testing module of the invention. The testing module of the invention further has at least four rods (53) respective located at corners of the first and the second plates (51,52), such that either the first plate (51) or the second plate (52) will not rotate with respect to the top plate (42).

The first plates (51) are securely mounted on the main shaft (43) and in parallel with each other. The second plates (52) mounted between two adjacent first plates (51) are slidable in relation to the main shaft (43). However, the last second plate (52) is securely mounted on the secondary shaft (44). Therefore, when the top plate (42) moves together with the first plates (51), the first plates (51) will gradually move toward the corresponding second plate (52). It is to be noted that the second plate (52) has a plurality of T-shaped slots (521) defined therein and each of which is spaced apart from the others. A plurality of supporting plates (61) are slidably secured on the second plate (52) with the assistance of a rectangular block (63) defining therein a through hole (631). The rectangular block (63) is confined by the T-shaped slot (521) for rotation after being received in the slot (521), such that a supporting plate (61) defining therein a screw hole (611) is able to be threadingly engaged with the rectangular block (63) by a bolt (62). With the arrangement of the supporting plates (51) and the rectangular blocks (63), each of the supporting plates (61) are able to be arranged in parallel. Furthermore, the first plate (51) has a plurality of inline through holes (511) defined to correspond to one of the plurality of T-shaped slots (521) and each of the through holes (511) have two slits (512) oppositely located with respect to each other, whereby two pins (513) are able to be respectively inserted into one of the slits (512). A plurality of pressing plates (64) are able to be adjustably secured with respect to the first plate (51). Each of the pressing plates (64) have a T-shaped cutout (641) defined in a top face thereof and two blind holes defined to correspond to the slits (512). With a retaining device (65) having a head (651), a neck (652) immediately adjacent to the head (651) and a body (653) integrally formed with the neck (652). The head (651) and the neck (652) are able to be received in the T-shaped cutout (641) and the body (653) is able to extend through the through hole (511) of the first plate (51). Thereafter, a nut (514) is used to threadingly secure the pressing plate (64) with respect to the first plate (51) and two pins (513)extend through the slits (512) and into the blind holes (643) of the pressing plate (64) to prevent rotation thereof. After each of the pressing plates (64) are secured to the first plate (51) and correspondingly located at a center of two adjacent supporting plates (61). The testing module of the invention is ready for testing the strength of the welding area between a plurality PCB (10) and surface mounted devices (11).

Figure 3:
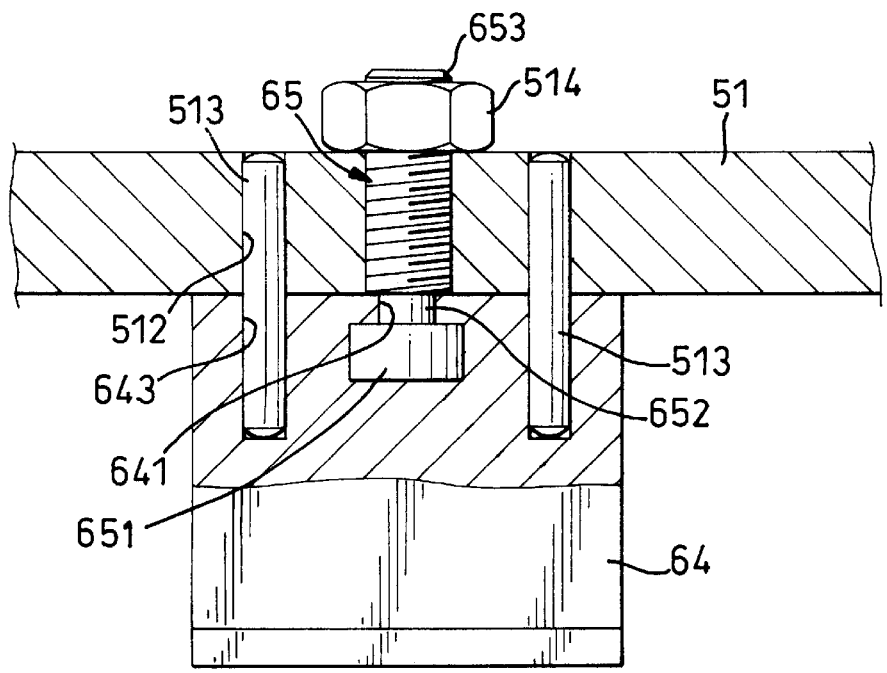
FIG. 3 is a partial cross sectional view showing the connection between the upper plate and the pressing plate.
Figure 4:
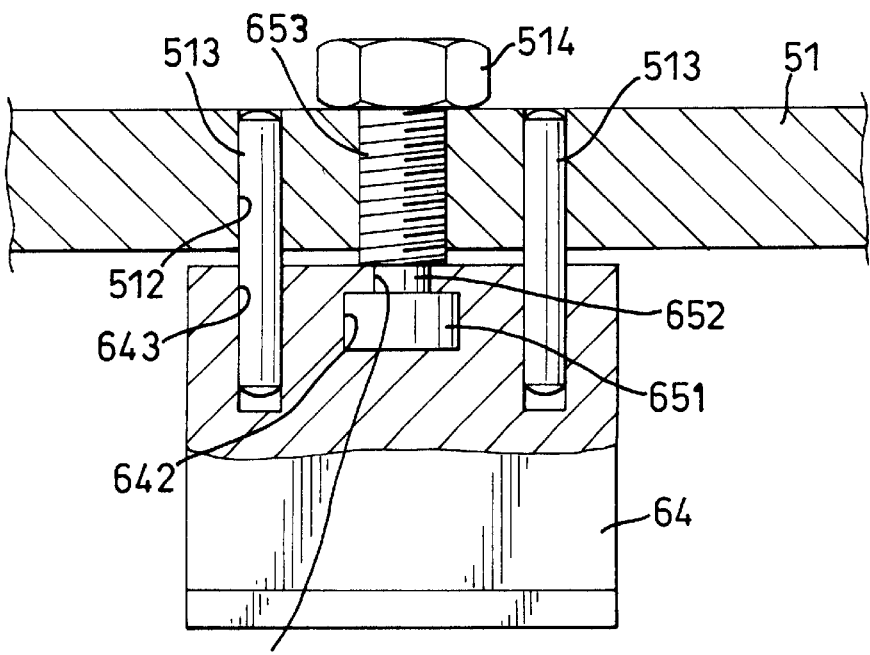
FIG. 4 is a partial cross sectional view showing the adjustment of the pressing plate in relation to the upper plate by the adjusting screw.
Figure 5:
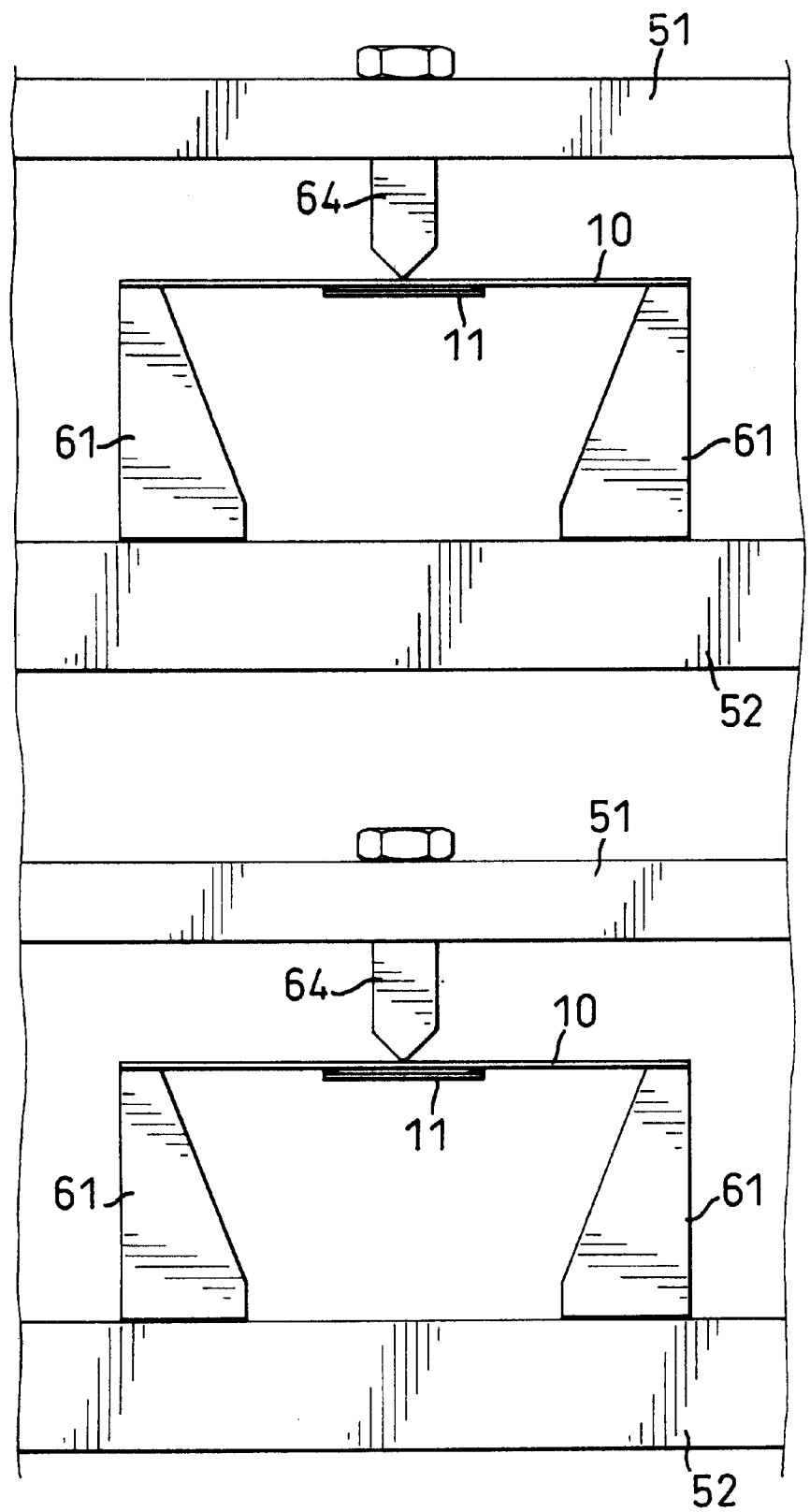
FIG. 5 is a plan view showing the arrangements of the supporting plates and the pressing plates.
Figure 6:
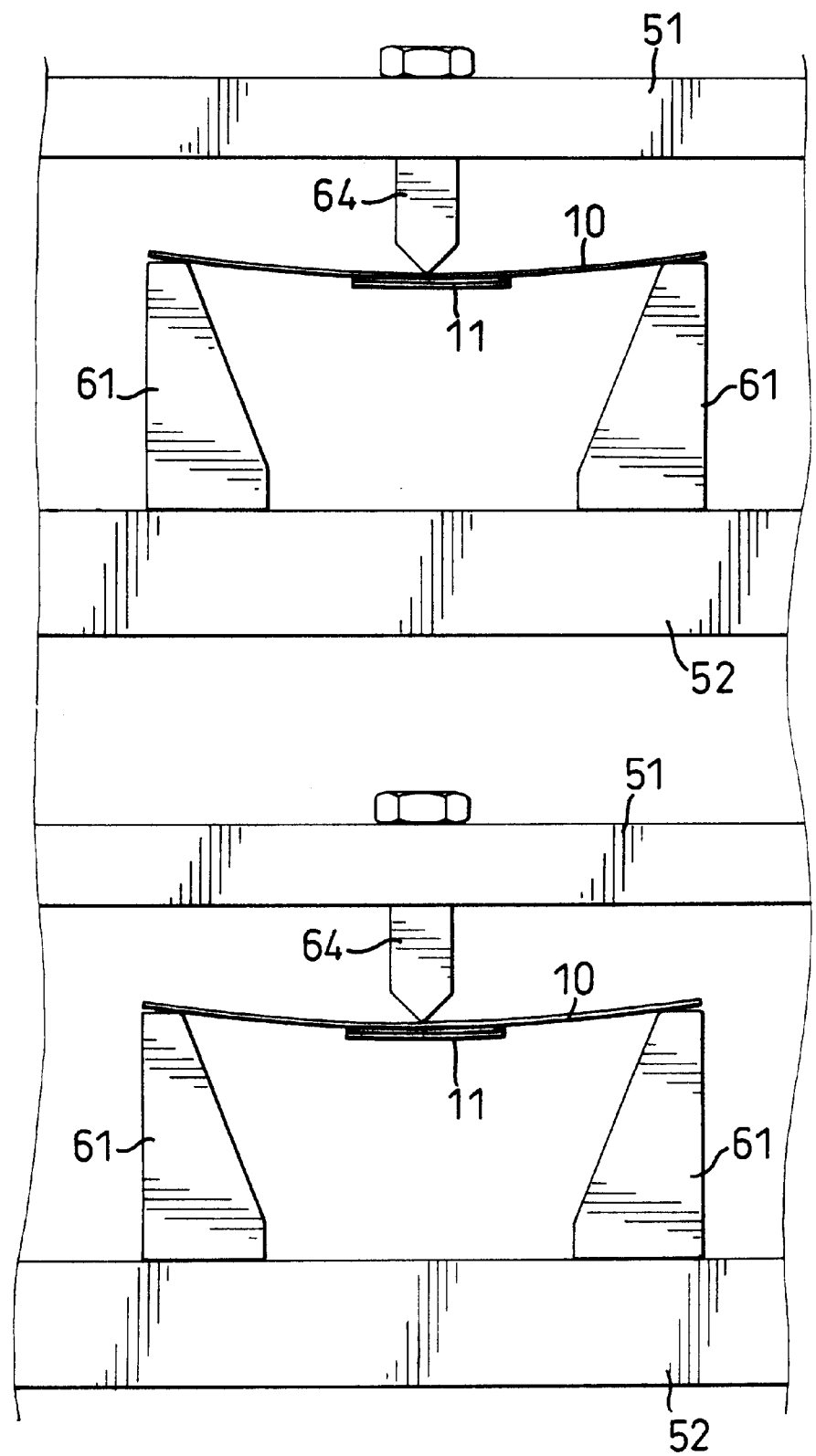
FIG. 6 is a plan view showing the movement of the pressing plates with respect to the supporting plate, such that a PCB supported by two adjacent supporting plates is able to be tested by the pressing plate for the strength of the contacting area between the PCB and the surface mounted device.
Figure 7:
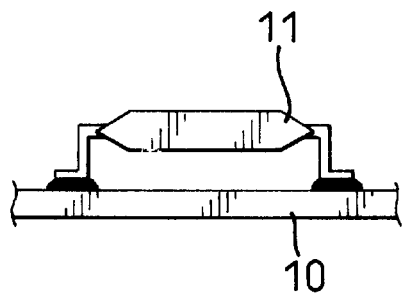
FIG. 7 is a schematic plan view showing the engagement between a PCB and a surface mounted die.
Figure 8:
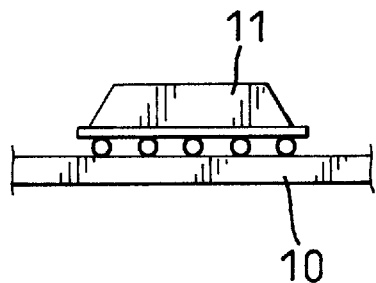
FIG. 8 is a schematic plan view showing the engagement between the PCB and the surface mounted device.
Figure 9:
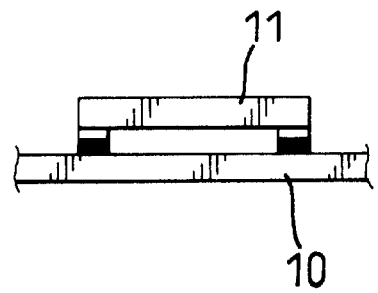
FIG. 9 is a schematic plan view showing the engagement between the PCB and the surface mounted device.
Figure 10:
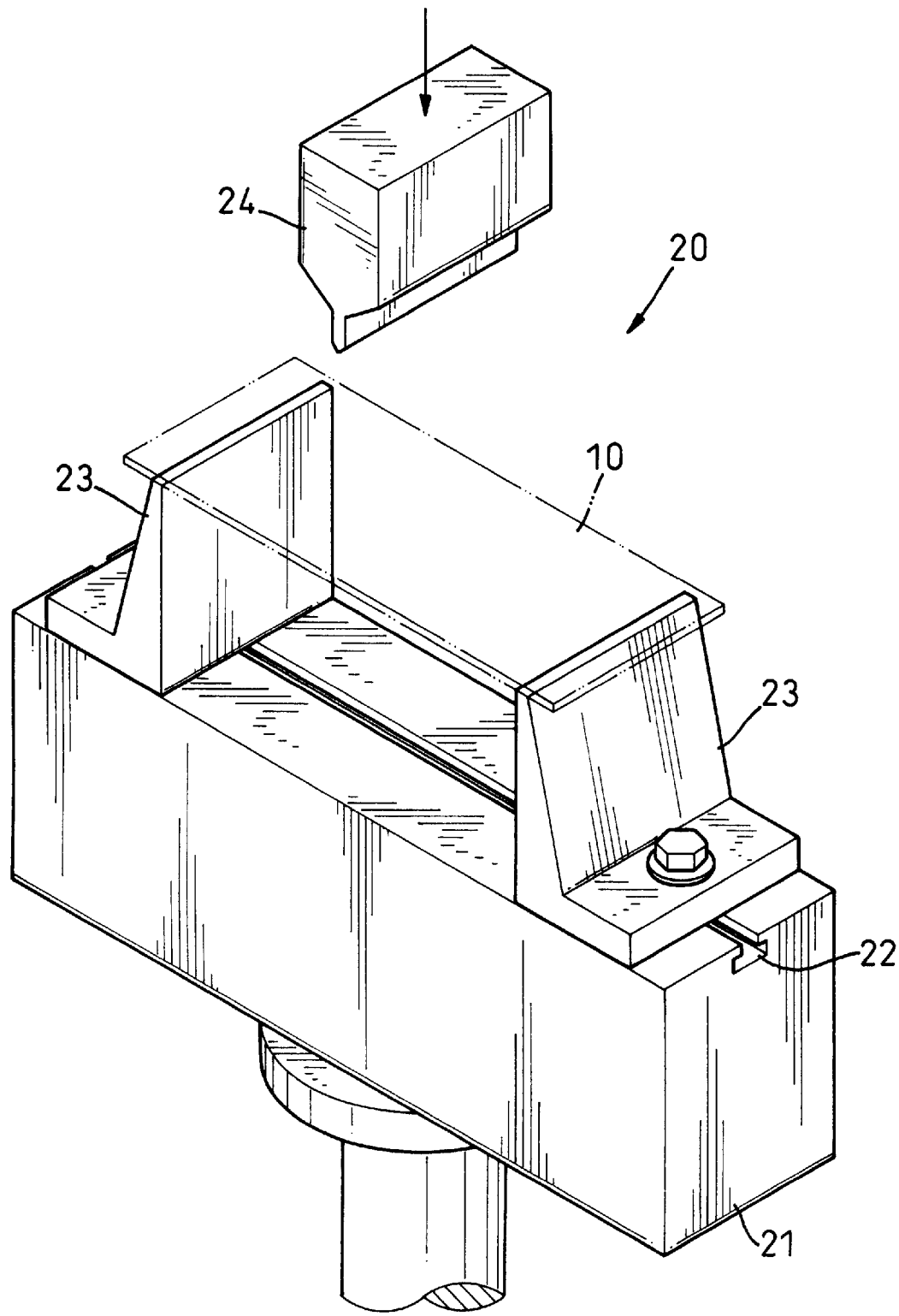
FIG. 10 is an exploded perspective view showing a conventional structure of a strength testing module.
Figure 11:
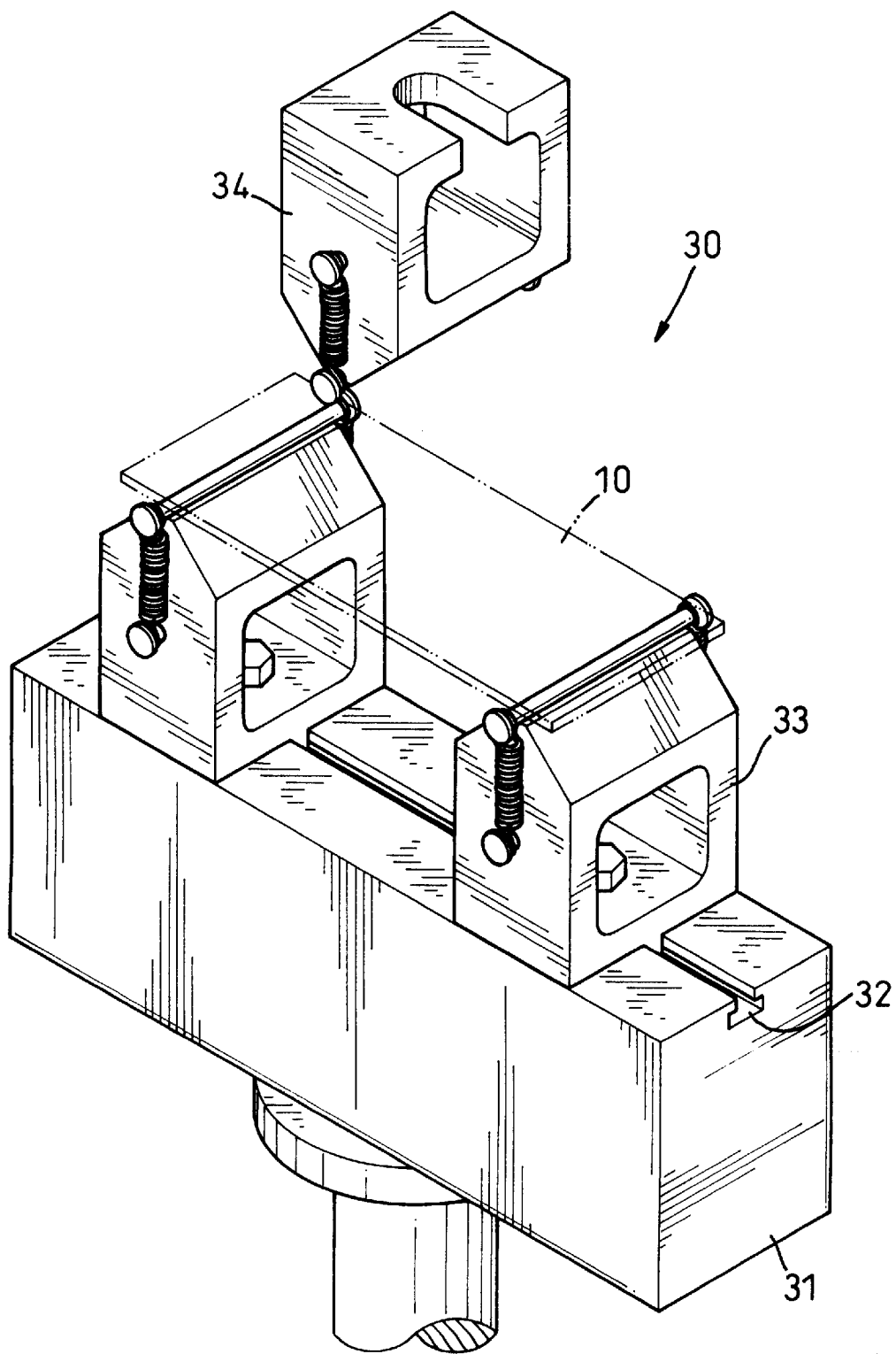
FIG. 11 is an exploded perspective view showing alternative embodiment of a conventional structure of a strength testing module.
Figure 12:
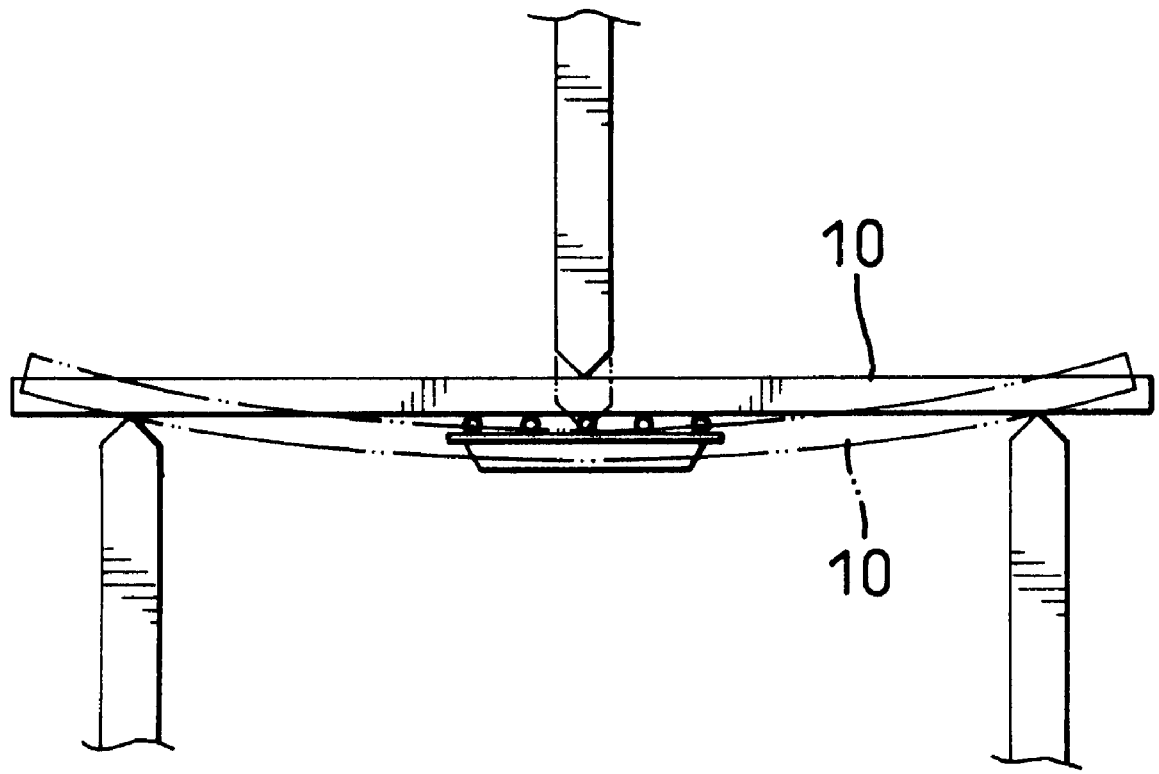
FIG. 12 is a schematic plan view showing the deformation of the PCB subjected by the movement of the pressing plate.

Referring to FIGS. 3 and 4, for further adjustment to the precision of the pressing plate (64), the pressing plate (64) is able to be adjusted by the rotation of the nut (514), such that the distance between the pressing plate (64) to the second plate (52) is changed. After adjustment to the pressing plates (64), the PCB (10) with the surface mounted device (11) welded thereunder is placed between two adjacent supporting plates (61), as shown in FIG. 5, such that the pressing plate (64) mounted on the first plate (51) and corresponded to the PCB (10) is able to proceed the strength test for adhesion of the surface mounted device (11) to the PCB (10).

From the previous description, it is concluded that the strength testing module is able to accomplish the testing to a plurality of PCBs (10) at a time, the efficiency of the testing is dramatically increased and therefore, the time for the test is also reduced.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A testing module for testing a welding area strength on a PCB, the testing module comprising:
    a plurality of first plates (51) securely mounted in parallel with respect to each other and having a plurality of pressing plates (64) adjustably mounted thereto; and
    a plurality of second plates (52) movably mounted in parallel with respect to the first plates (510 and having a plurality of supporting plates (61) securely mounted thereon;
    wherein each of the pressing plates (64) are mounted at a location corresponding to a center position between a pair of adjacent supporting plates (61).

2. The testing module as claimed in claim 1 further having a base (40) provided with two posts (41) integrally extended outward therefrom and a top plate (42) slidably mounted between the two posts (41) and provided with a main shaft (43) securely extending out therefrom so as to have the plurality of first plates (51) securely mounted thereon and the plurality of second plates (52) movably mounted thereon.

3. The testing module as claimed in claim 2, wherein each of the second plate (52) have a plurality of slots (521) defined therein and the first plates (51) have a plurality through holes (511) defined to correspond to one of the slots (521).

4. The testing module as claimed in claim 3, wherein the pressing plates (64) have a cutout (641) defined therein and corresponded to one of the through holes (511) of the first plate (51) thereby allowing the pressing plates (64) to be adjustably mounted on the first plate (51).

5. The testing module as claimed in claim 4, including a retaining device (65) having a head (651), and a neck (652) integrally formed with the head (651) and a body (653) which is used to adjustably secure the pressing plates (64) to the first plate (51) by inserting the head (6510 and the neck (652) into the cutout (641) and extending the body (653) into one of the through holes (511) to be threadingly connected with a nut (514)

6. The testing module as claimed in claim 5, wherein two slits (512) are defined around each one of the through holes (511) and opposite to each other; and
    wherein two blind holes (643) are defined beside the cutout (641) and corresponding to the two slits (512) thereby allowing two pins (513) to be inserted through the slits (512) and into the blind holes (643) after the pressing plates (64) are secured in relation to the first plate 51.

7. The testing module as claimed in claim 3, wherein each of the slots (521) is T-shaped.

8. The testing module as claimed in claim 7, wherein a plurality of rectangular blocks (63) are provided to be slidably received in the T-shaped slot (521) to respectively correspond to one of the plurality of supporting plates (61).

9. The testing module as claimed in claim 8, wherein each of the supporting plates (61) have a through hole (611) defined therethrough and sa bolt (620 is provided to be threadingly inserted through the through hole (611) and into one of the rectangular blocks (63) to secure the supporting plate (61) with respect to the second plate (52).

10. The testing module as claimed in claim 2, wherein a secondary shaft (44) is provided to the base (40) and securely connected with a second plate (52) on a top thereof.

* * * * *